United States Patent
Fayram et al.

[11] Patent Number: 5,983,472
[45] Date of Patent: Nov. 16, 1999

[54] CAPACITOR FOR AN IMPLANTABLE CARDIAC DEFIBRILLATOR

[75] Inventors: Timothy A. Fayram, Gilroy; Benjamin D. Pless, Atherton, both of Calif.; Scott McCall, Six Mile, S.C.; Craig Mar, Fremont, Calif.

[73] Assignee: Pacesetter, Inc., Sunnyvale, Calif.

[21] Appl. No.: 08/969,074

[22] Filed: Nov. 12, 1997

[51] Int. Cl.⁶ .............................. H01G 7/00; H01G 4/38
[52] U.S. Cl. .................. 29/25.42; 29/25.41; 29/25.03; 29/412; 361/301.4; 361/329
[58] Field of Search ..................... 607/5; 29/25.03, 29/25.41, 25.42, 830, 847, 412, 416, 467; 361/301.4, 329, 508, 528

[56] References Cited

U.S. PATENT DOCUMENTS

| | | | |
|---|---|---|---|
| 1,973,694 | 9/1934 | Briggs et al. | 29/25.03 |
| 2,512,688 | 6/1950 | Skog | 29/412 |
| 3,832,607 | 8/1974 | Obenchain et al. | 29/25.42 |
| 3,854,181 | 12/1974 | Matsuwake et al. | 29/25.41 |
| 4,437,139 | 3/1984 | Howard | 29/25.42 |
| 5,230,712 | 7/1993 | Matthews | 29/25.03 |
| 5,253,148 | 10/1993 | Katsu | 29/25.03 |
| 5,522,851 | 6/1996 | Fayram | 607/5 |
| 5,660,737 | 8/1997 | Elias et al. | 216/6 |
| 5,758,398 | 6/1998 | Rijnbeek et al. | 29/25.42 |
| 5,814,082 | 9/1998 | Fayram et al. | 607/5 |

*Primary Examiner*—Lee Young
*Assistant Examiner*—A. Dexter Tugbang
*Attorney, Agent, or Firm*—Steven M. Mitchell

[57] ABSTRACT

A method of manufacturing a capacitor for use in an implantable cardiac defibrillator by forming a set of conductive sheets with the same profile having a sacrificial portion. An alignment figure is formed in each sheet, and the sheets are stacked and aligned by registering the alignment figures with each other. The sacrificial portions are removed from each of the sheets, which are secured together and positioned in a capacitor housing. Each sheet may include two major portions joined by the sacrificial portion, so that each major portion may become part of a separate capacitor stack after the sacrificial portion is removed, doubling manufacturing throughput.

16 Claims, 11 Drawing Sheets

CAPACITOR FOR AN IMPLANTABLE CARDIAC DEFIBRILLATOR

FIELD OF THE INVENTION

The invention relates to capacitors, and more particularly to capacitors for implantable cardiac defibrillators.

BACKGROUND AND SUMMARY OF THE INVENTION

Defibrillators are implanted in patients susceptible to cardiac arrhythmias or fibrillation. Such devices provide cardioversion or defibrillation by delivering a high voltage shock to the patient's heart, typically about 500–750V. High voltage capacitors are used in defibrillators to accumulate the high voltage charge following detection of a tachyarrhythmia. It is desirable to make implantable devices as small as possible, with slim, flat packages being desired for pectorally implanted defibrillators. Therefore, flat capacitors have been developed to avoid the disadvantages of traditional cylindrical aluminum electrolytic capacitors.

Such a flat capacitor is disclosed in U.S. Pat. No. 5,522,851 to Fayram, which is incorporated herein by reference. Flat capacitors include a plurality of layers laminarly arranged in a stack. Each layer includes an anode and a cathode, with the anodes and cathodes being commonly connected to respective connectors. The layers may be cut in nearly any shape, to fit within a similarly shaped housing designed for a particular application. The capacitance of such a device is proportional to the number of layers, and to the area of each layer, providing significant design flexibility. However, it is desirable to further improve the capacitance per unit volume ratio of current devices, which currently devote some volume to clearances for preventing shorting of components, and to fastening and alignment elements for securing the device components to each other.

In addition, the process of manufacturing such capacitors is very labor intensive. The layer by layer assembly requires great care by the assembler to avoid damaging or misaligning any of the layers. The registration holes used in some devices aid manufacturing efficiency, but decrease the capacitance per unit volume and thus, the stored energy per unit volume.

The present invention overcomes the limitations of the prior art by providing a method of manufacturing an implantable cardiac defibrillator by forming a set of conductive sheets with the same profile having a sacrificial portion. An alignment figure is formed in each sheet, and the sheets are stacked and aligned by registering the alignment figures with each other. The sacrificial portions are removed from each of the sheets, which are secured together and positioned in a capacitor housing. Each sheet may include two major portions joined by the sacrificial portion, so that each major portion may become part of a separate capacitor stack after the sacrificial portion is removed, doubling manufacturing throughput.

DETAILED DESCRIPTION OF A PREFERRED EMBODIMENT

Figure 1:
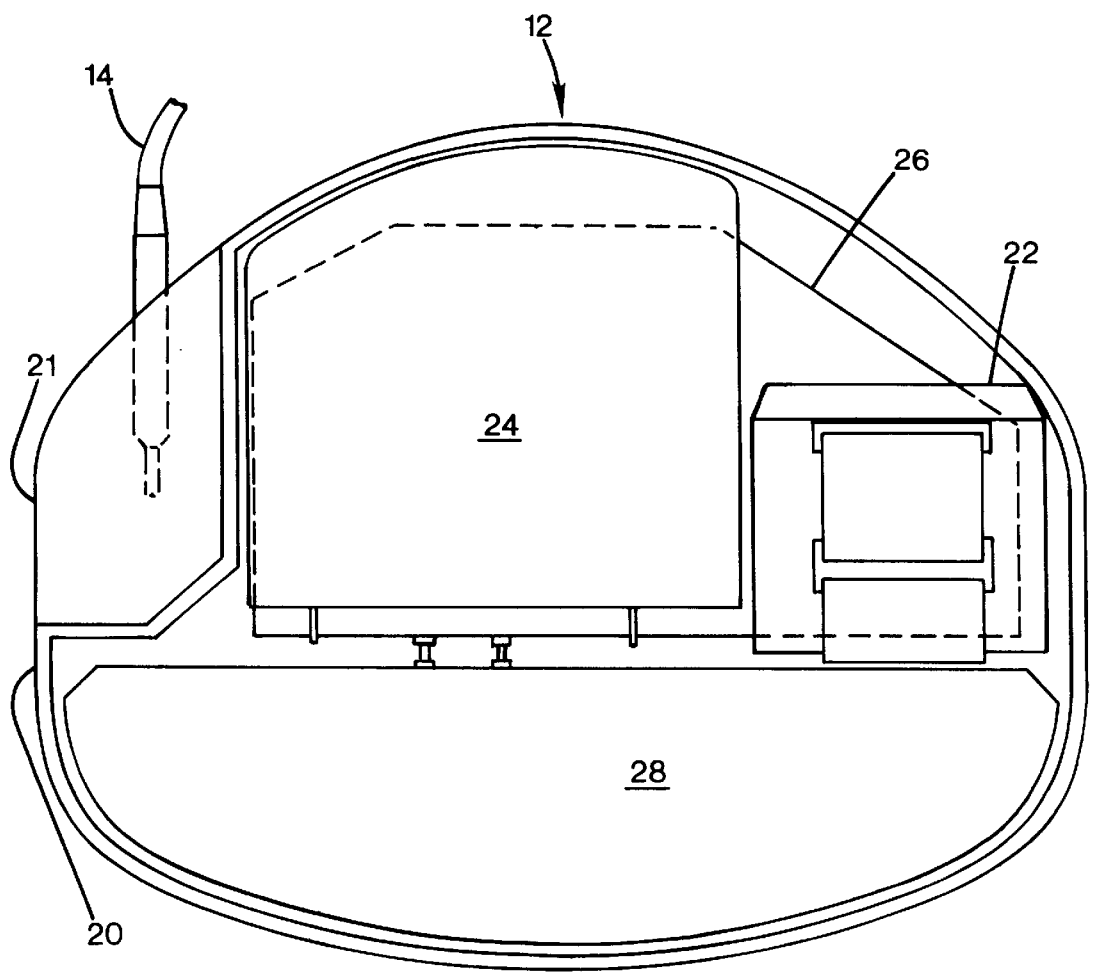
FIG. 1 shows an implantable defibrillator having capacitors according to the present invention.

FIG. 1 illustrates a defibrillator 12 for pectoral implantation. A single pass endocardial lead set 14 extends from the unit, through the patient's subclavian vein, and into the patient's heart. The defibrillator 12 includes an outer housing 20 that includes a connector portion or header 21 for attachment of the lead set 14. The housing 20 contains a transformer 22, a battery 24, printed circuit assembly 26, and two capacitors 28 (only one shown.) The battery provides low voltage electrical energy that is converted by transformer 22 to charge the capacitor when needed so that they may provide a high voltage shock. The printed circuit assembly 26 connects to the lead set 14 so that it may sense and analyze electrical signals from the heart, and control the delivery of an appropriate therapy such as a high voltage shock.

Figure 2:
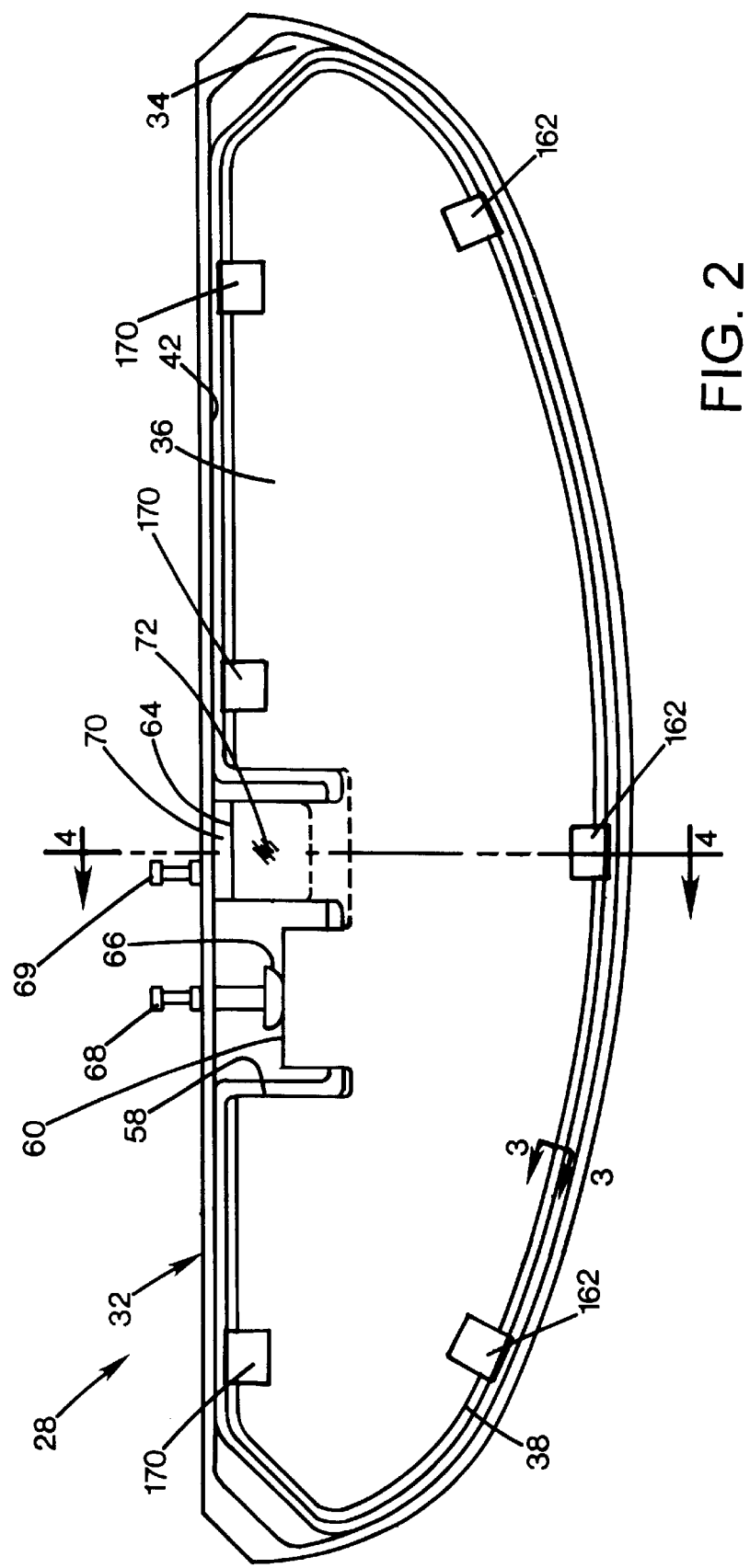
FIG. 2 is a plan view of the interior of the capacitor of FIG. 1.

FIG. 2 illustrates in detail the construction of the capacitor 28, which may be designed as virtually any flat shape to conform to a desired housing shape. The capacitor includes a metallic housing 32 defining a chamber 34, in which resides a capacitor stack 36. Housing 32 may alternatively be plastic. The capacitor stack has a periphery 38 that includes a cutout connection region 58 discussed below. The remaining major portion of the periphery has gently curved convex portions, and straight portions. The overall periphery of the stack is defined as the edge of the layers or sheets that extend farthest at a particular location.

Figure 3:
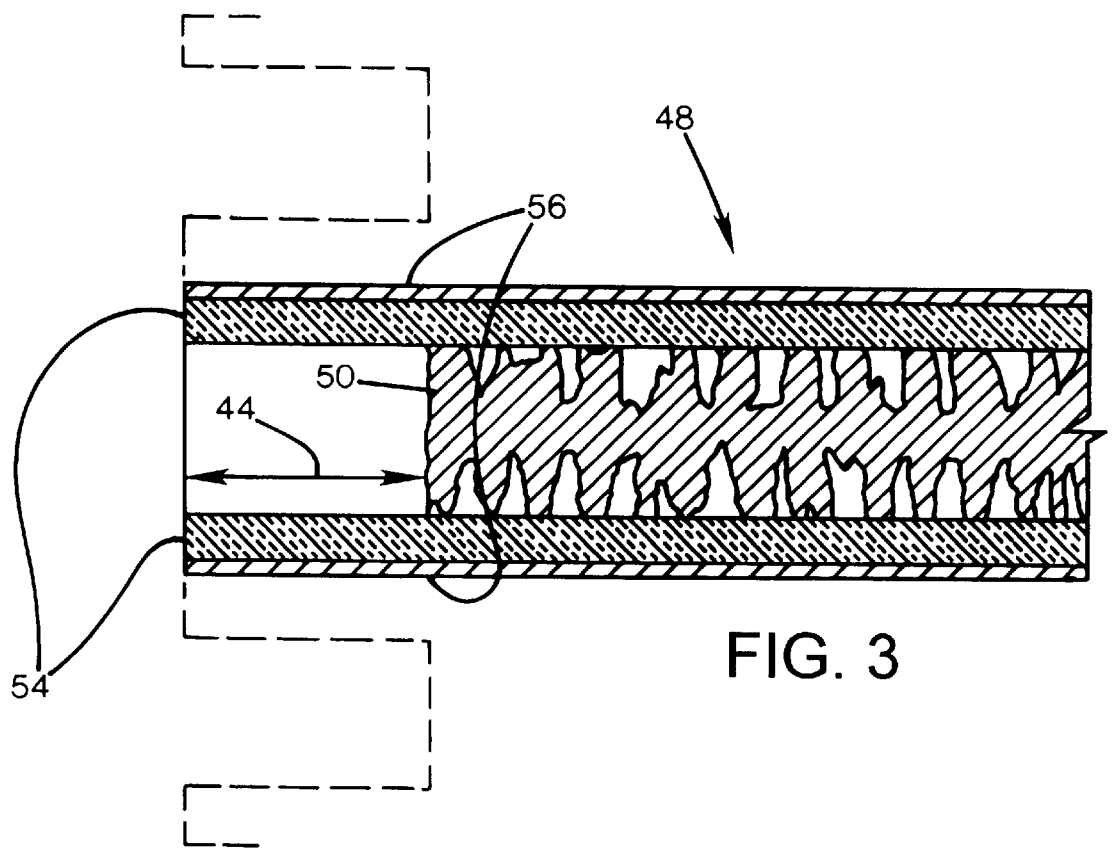
FIG. 3 is a cross sectional side view of a single capacitor layer taken along line 3—3 of FIG. 2.

As shown in FIG. 3, the capacitor stack 36 is formed of a number of essentially identical flat capacitor layers 48 whose electrical elements are connected in parallel. The number of layers determines the capacitance and thickness of the device; in the preferred embodiment, 12 layers are used. Each layer 48 is a sandwich of sheets: a central anode 50 that is highly etched on both major surfaces and a pair of separator sheets 54 (typically paper) covering a pair of aluminum cathode foil sheets 56 and positioned on the opposite sides of the anode. Only a single cathode foil sheet 56 is positioned between the separator sheets 54 in adjacent layers 48 of the capacitor stack 36. Thus, the sequence in the stack 36 is: anode sheet, separator sheet, cathode sheet, separator sheet, anode sheet, etc. In the preferred embodiment, the anode 50 consists of two sheets, each approximately 0.004 inch thick and stacked together. Single, double, triple and even higher multiples of anode sheets may be used. Each separator sheet is typically 0.001 inch thick, and each cathode sheet is 0.0008 inch thick. The separator sheet may be a single paper sheet or may comprise multiple sheets.

The etched anode layer can be "formed" by passing a current through the anode in the presence of an electrolyte.

This generates an oxide layer that functions as a dielectric. The forming is typically done before assembly of the stack. Once the capacitor is assembled, an electrolyte is injected into the chamber through a hole in the housing which is then sealed.

As shown in FIG. 3, at the major portion of the stack periphery, the paper sheets 54 and cathode sheets 56 extend beyond the anode sheet 50 by a separation distance 44 to prevent contact between the cathode and anode due to any misalignment. The separation distance is preferably about 0.030 inch (0.75 mm) (but may be as small as 0.01 inch), which is sufficiently large to avoid contact, and is sufficiently small to avoid excessively reducing the capacitance of the device, as the extending portions of the cathode do not contribute to the device capacitance. To provide effective isolation, the separator layers 54 extend the full separation distance, so that the smallest distance between respective exposed conductive portions of the cathode and anode are separated by the full separation distance. The separating paper layers 54 also serve as a repository for the electrolyte between the anode and cathode layers.

Referring back to FIG. 2, each of the layers 48 has a cutout region 58 at its periphery, with the cutouts of each layer being aligned when the sheets are installed in the housing to provide space for electrical connections. The anodes 50 include anode tabs 60 extending into the cutout in registration with each other. Similarly, the cathodes 56 include cathode tabs 64 that extend into the cutout region and registered with each other, but spaced apart from the anode tabs by at least the separation amount to allow separate connection without contacting. The paper spacers 54 do not extend fully into the cutout, but extend only by at least the separation amount to prevent contacting. Therefore, the free ends of the cathodes, like the anodes, may be connected together in parallel when the tabs are brought together in a bundle.

Figure 4:
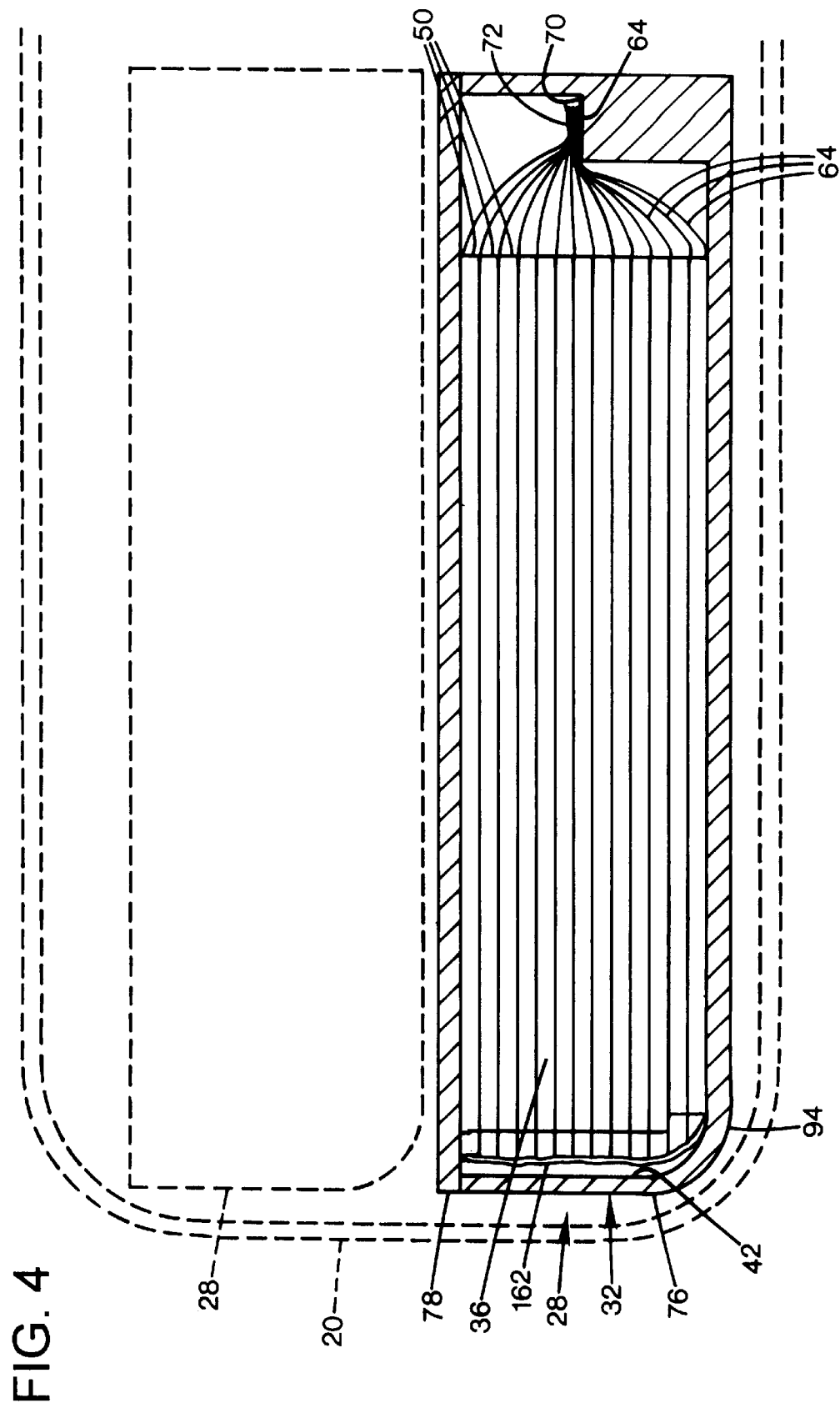
FIG. 4 is a cross sectional side view of a single capacitor layer taken along line 4—4 of FIG. 2.

After all layers have been assembled into a stack by the method discussed in detail below, the stack with anode tab and anode pin 68 is then installed in the housing. The anode pin 68 is electrically insulated from the housing. The cathode tabs 64 are electrically connected to the capacitor housing. A cathode lead 69 provides an external electrical connection to the housing. The cathode tabs 64 are ultrasonically welded to a housing step 70 abutting the periphery of the interior of the housing. As shown in FIG. 4, the step height is about half the height of the stack 36, so that the top and bottom cathode sheets need not be excessively deflected. An ultrasonic tool compresses the cathode tabs against the step at a weld point 72, and imparts ultrasonic energy to provide a secure electrical and mechanical connection.

As further shown in FIG. 4, the housing 32 of each capacitor 28 includes a case 76, and a flat lid 78 overlaying the case and resting on the case's upper rim. The lid is attached and the housing sealed to prevent loss of electrolyte solution from the housing. This is achieved by laser welding the entire periphery of the lid while maintaining pressure on the lid.

After aging and testing, two capacitors are installed in a single defibrillator unit. The capacitors are stacked with their lids facing in the same direction. Because the defibrillator housing 20 has radiused edges for a physiologic shape appropriate to an implanted device, the capacitor housing has a 0.070 inch radiused edge 94 about a portion of its lower periphery. This permits the lower of the capacitors to efficiently fill the defibrillator housing 20. So that the capacitor layers efficiently fill the capacitor housing, the lowest two layers may have reduced peripheries to avoid abutting the radius. The remaining layers extend closer to the housing wall to maximize capacitance for a given housing volume, with the preferred spacing being about 0.040 inch.

Figure 5:
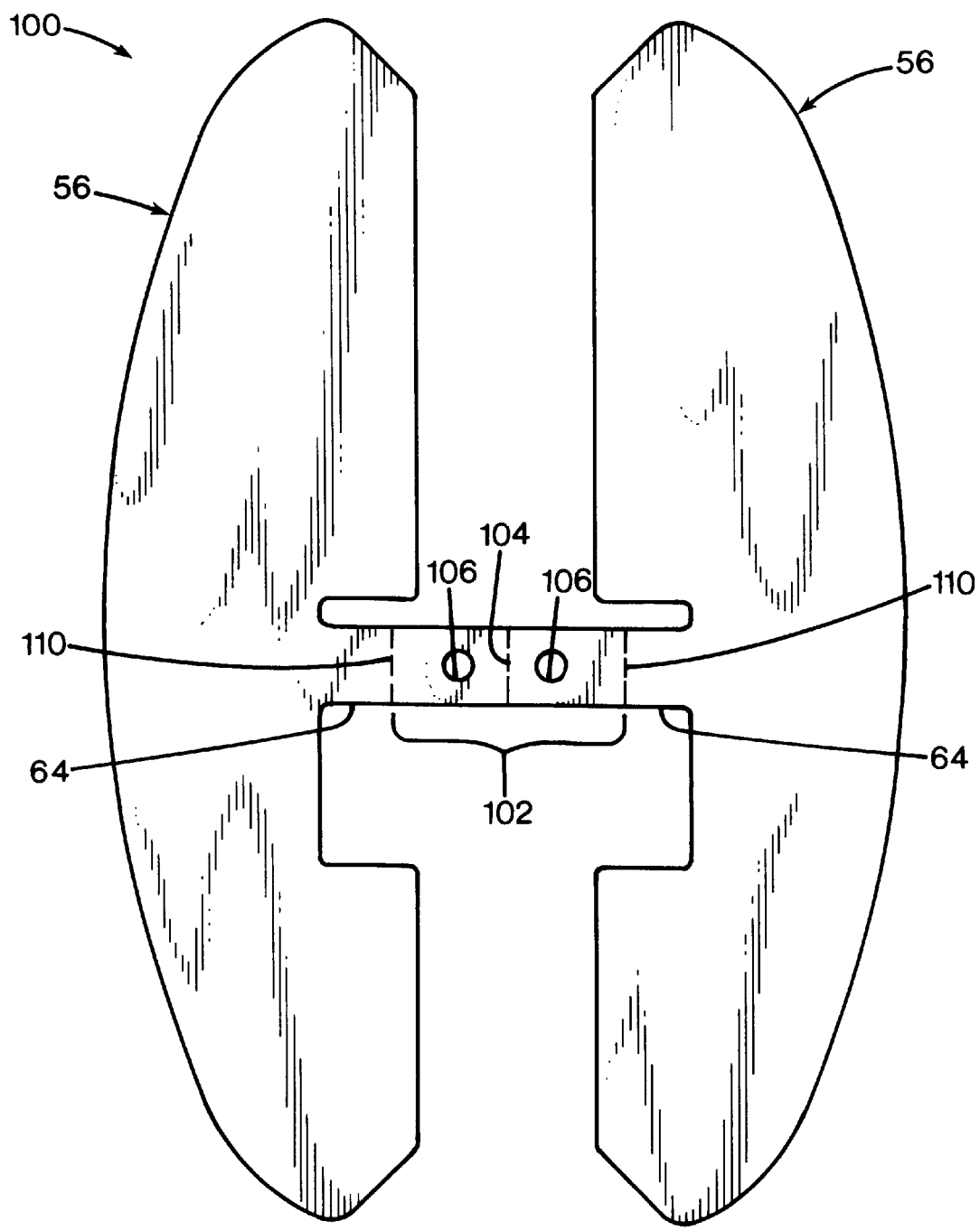
FIG. 5 is a plan view of a cathode layer according to a preferred embodiment of the invention.

FIG. 5 shows a cathode layer 100 having two symmetrically identical cathode sheet portions 56 joined together by a sacrificial cathode portion 102 extending between the cathode tabs 64. The sacrificial cathode portion is bisected by a center line 104 that forms a line of symmetry for the entire integral cathode layer 100. A pair of cathode alignment hole 106 are located on opposite sides of the center line on the sacrificial portion. A cathode tab end line 110 lateral of each hole 106 defines the ends of the sacrificial portion 102.

Figure 6:
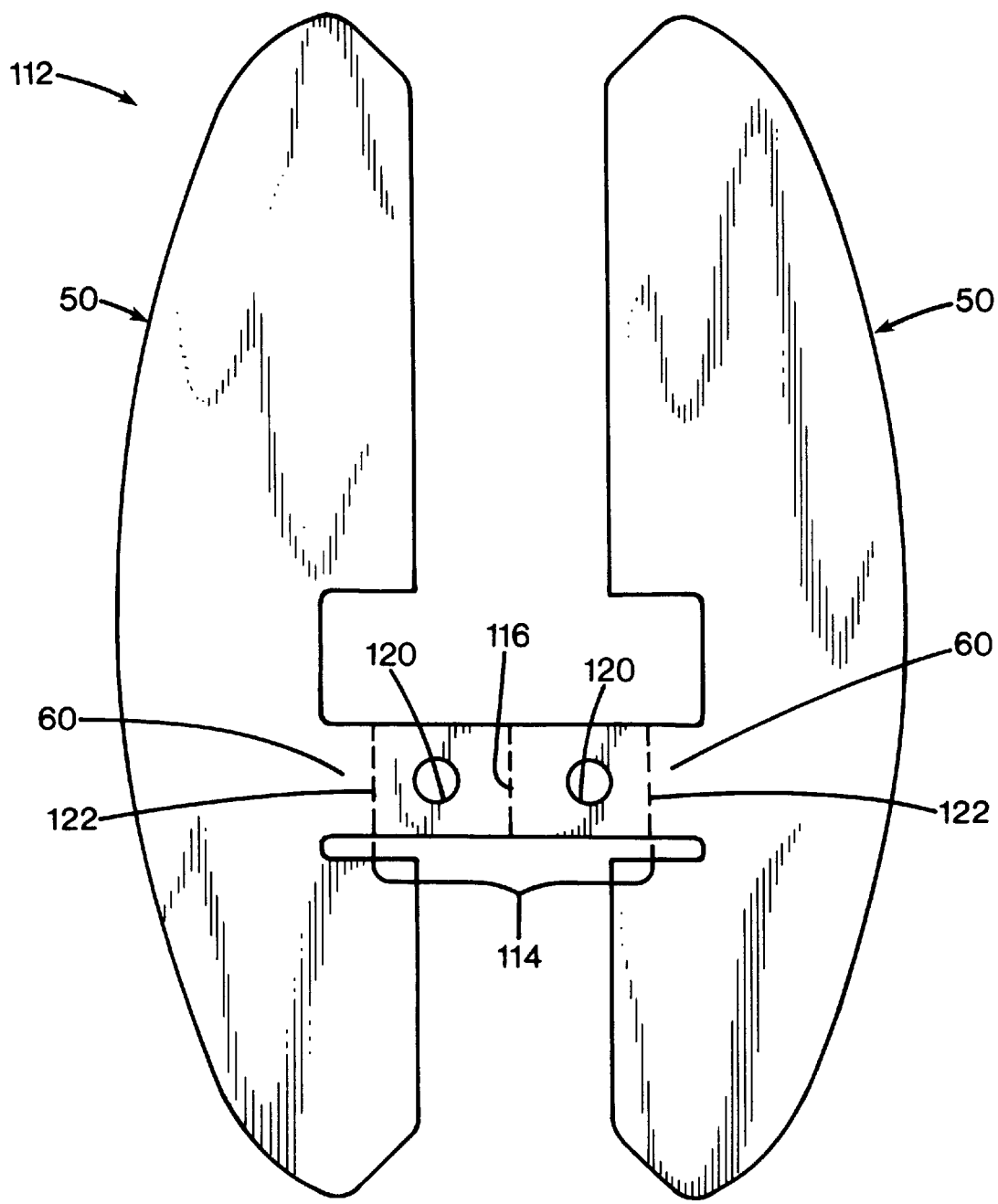
FIG. 6 is a plan view of an anode layer according to a preferred embodiment of the invention.

FIG. 6 shows an anode layer 112 having two symmetrically identical anode sheet portions 50 joined together by a sacrificial anode portion 114 extending between the anode tabs 60. The sacrificial anode portion is bisected by a center line 116 that forms a line of symmetry for the entire integral anode layer 112. A pair of anode alignment hole 120 are located on opposite sides of the center line on the sacrificial portion. An anode tab end line 122 lateral of each hole 120 defines the ends of the sacrificial portion 114.

Figure 7:
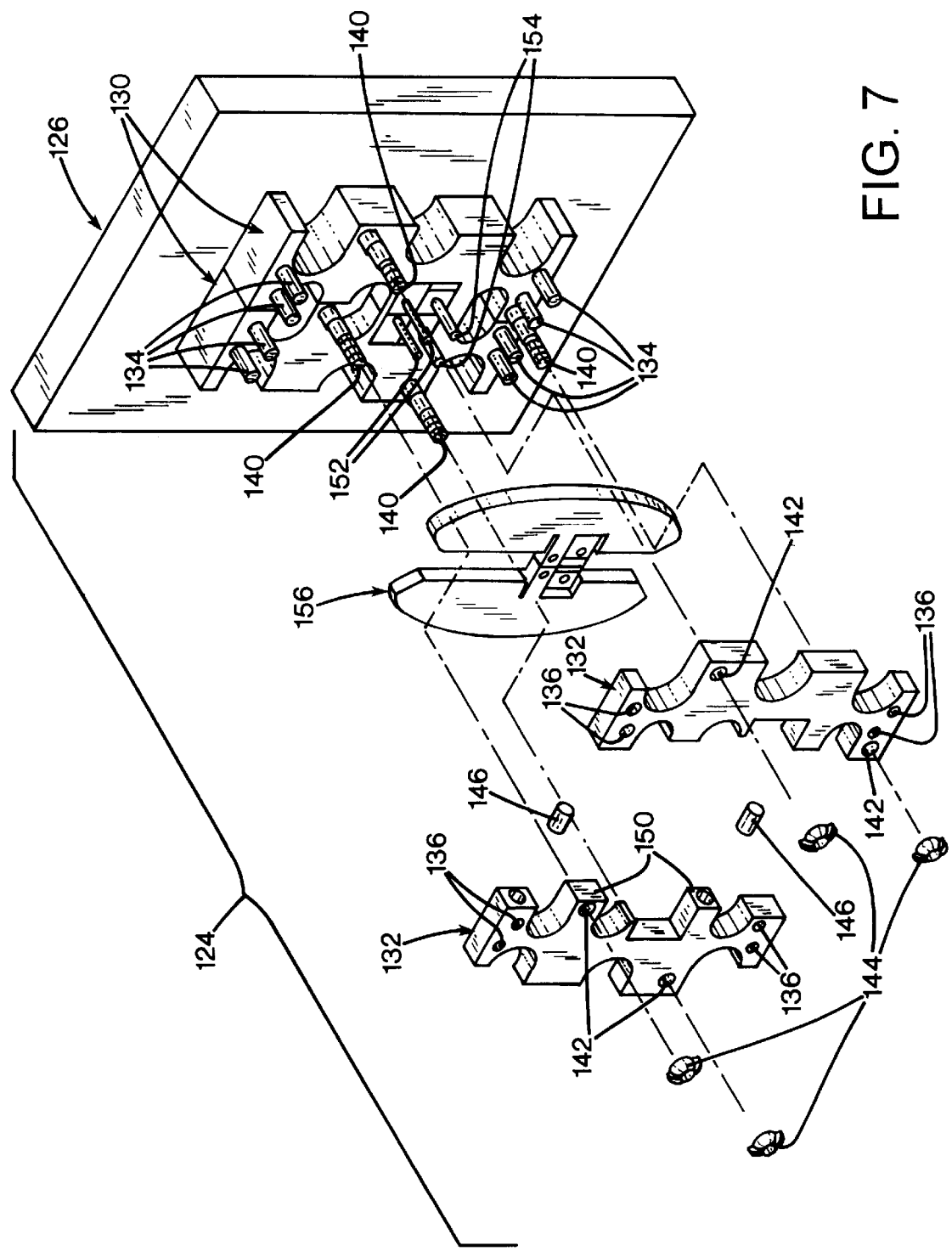
FIG. 7 is an exploded view of an assembly fixture according to a preferred embodiment of the invention.

FIG. 7 shows a manufacturing fixture 124 for stacking, aligning, clamping, taping, and welding the capacitor stack. The fixture has a rigid mounting plate 126 with a symmetrical pair of removable base elements 130. A pair of similar clamp elements 132 is removably securable to the corresponding base elements. Each base element has a set of clamp alignment pins 134 that are closely received by a corresponding set of alignment holes 136 on each of the clamps 132. A pair of threaded bosses 140 on each base 130 extends through corresponding clearance holes 142 on the clamps 132, for engagement by locking wing nuts 144 to bias each clamp against the corresponding base. Each of a pair of clamp registration pins 146 is received in a medial facing bore 150 on each clamp, at either end of the clamps, to ensure that the clamps are maintained in a coplanar arrangement to facilitate even clamping forces with the clamps as nearly parallel to the bases as possible. The clamp alignment pins 134 and threaded bosses 140 are positioned to be just outside of the domain of the capacitor sheets, so that capacitance-reducing through holes in the sheets are not required.

A pair of cathode alignment pins 152 protrudes from the base at the desired positions of the cathode alignment holes 106, and a pair of anode alignment pins 154 protrudes from the base at the desired positions of the anode alignment holes 120. The capacitor stack 156 is positioned between the bases and the clamps, with the alignment holes receiving the alignment pins 152, 154.

In the assembly process, the bases 130 are mounted to the plate 126, and the cathode, anode, and paper insulating layers are sequentially placed onto the bases in registration with the appropriate alignment pins to form the capacitor stack. In the exploded view shown, the stack is shown as assembled prior to installation on the bases; in the preferred method of manufacturing, the stack is formed sheet by sheet as the layers are mounted to the bases.

Figure 8:
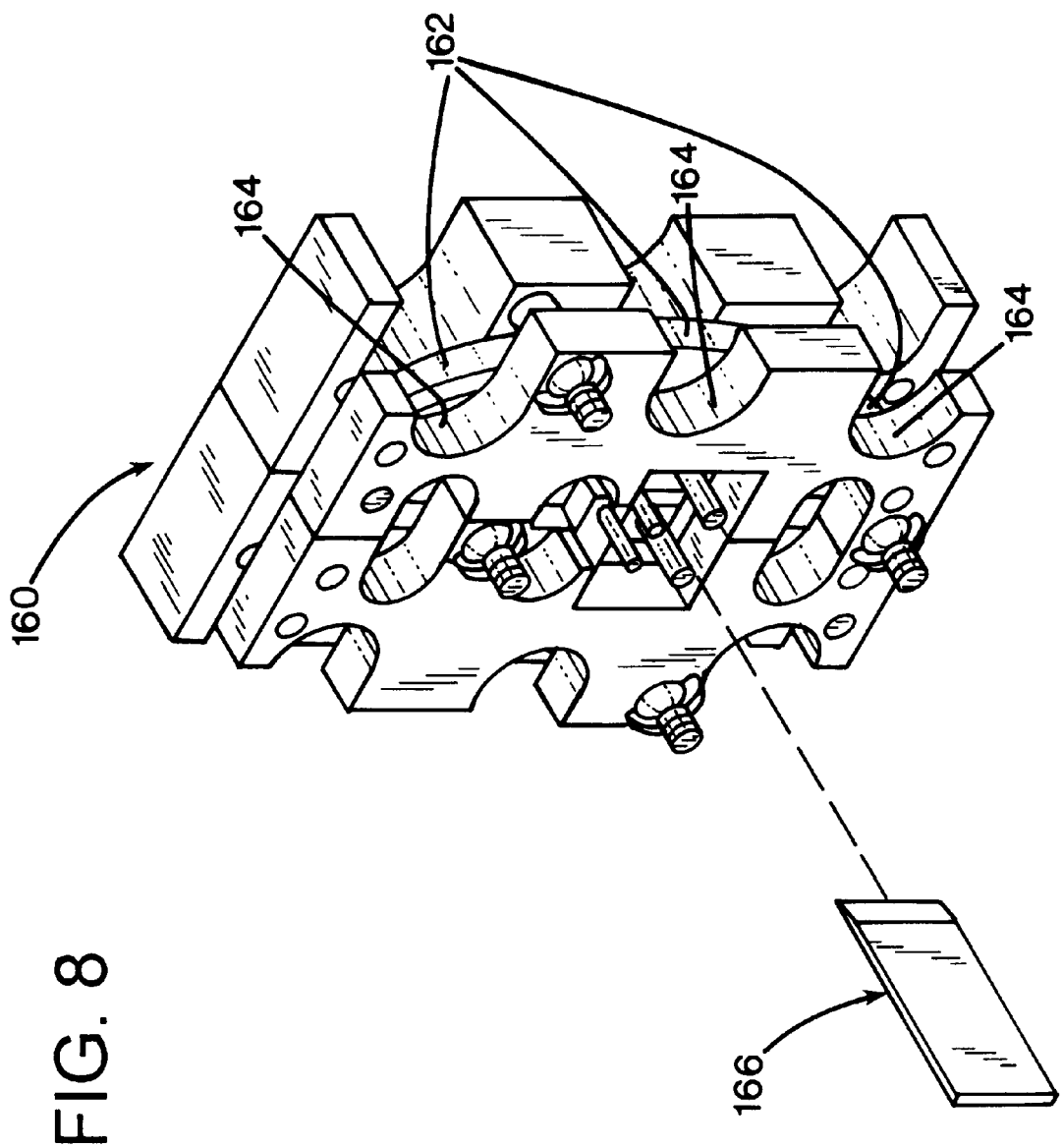
FIG. 8 is a perspective view of an assembly fixture according to a preferred embodiment of the invention.

After all sheets are installed on the proper sequence, the clamps are secured to the bases to bias the sheets together with even, parallel forces, forming a base/clamp assembly 160 that is removed from the mounting plate without disturbing the alignment of the layers of the capacitor stack, as shown in FIG. 8. Selected peripheral portions of the stacks are taped with insulating tape strips 162 to provide an insulative spacer from the interior walls of the capacitor housing, and to maintain mechanical alignment during subsequent manufacturing steps. The clamps are provided with peripheral cutouts 164 for this purpose.

Figure 9:
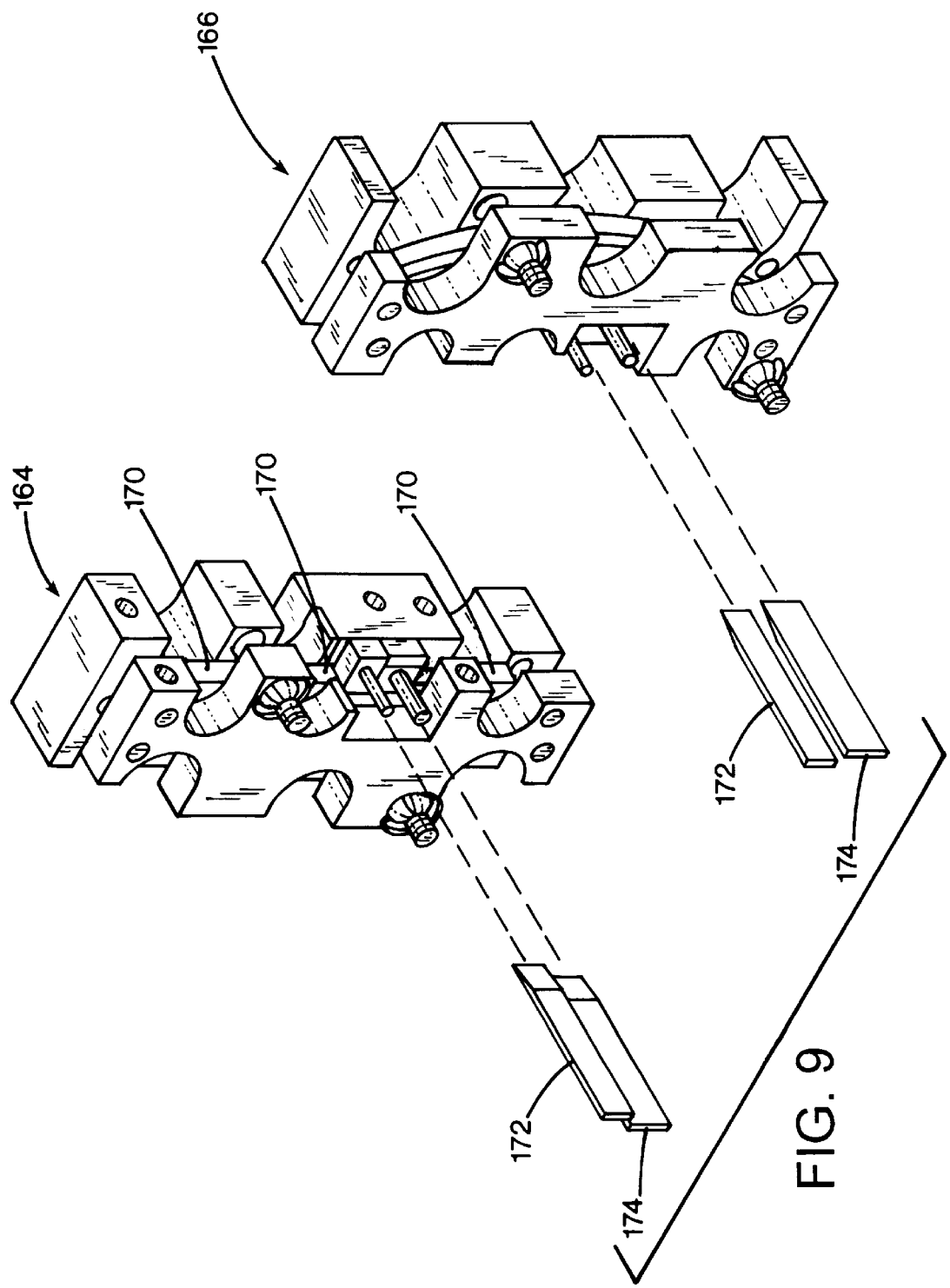
FIG. 9 is a perspective view of an assembly fixture according to a preferred embodiment of the invention.

After taping, a linear shear 166 cuts the cathode sheets at center line 104, and the anode sheets at center line 116. This permits the base/clamp assembly 160 to be separated into two halves 164, 166 as shown in FIG. 9. Additional medial portions of the stack peripheries are now made accessible for additional tape strips 170. The sacrificial portions of anode and cathode tabs are cut to final dimensions by trimmers 172, 174, and the stacks may be released from the clamps for installation in the capacitor housings as noted above. The anode tabs 60 are compressed together and welded together at their free ends, such as with a YAG laser. A tab of pure aluminum is welded to the anodes and to the anode pin. Optionally, the ends of the anode tabs may be welded together while the stack is still clamped, providing additional mechanical security against misalignment prior to installation in the housing. Alternatively, the cutting step may be performed by a laser that simultaneously welds and cuts the tabs to length.

Figure 10:
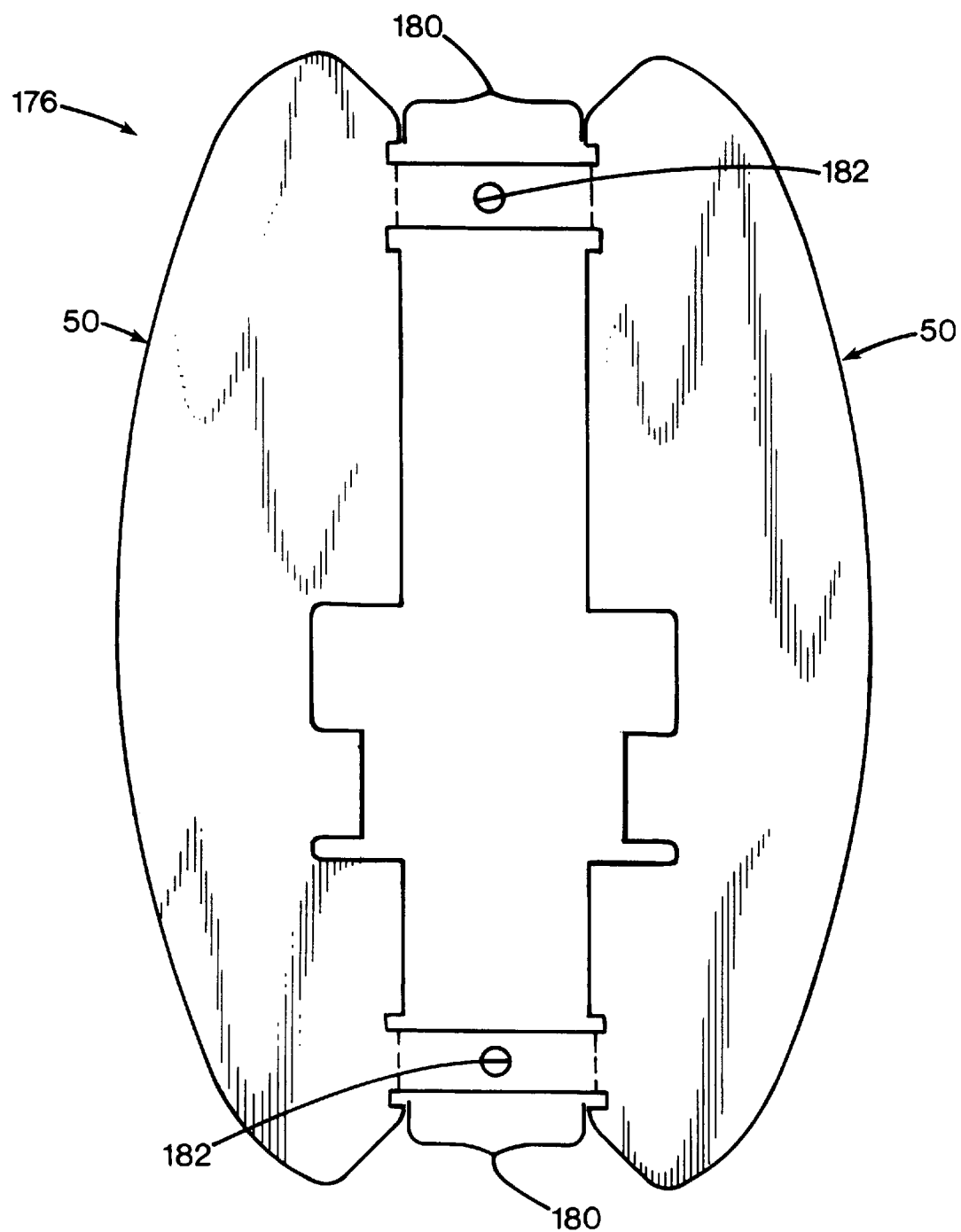
FIG. 10 is a plan view of a capacitor layer according to an alternative embodiment of the invention.

FIG. 10 shows an alternative anode sheet 176 having a pair of widely spaced apart sacrificial portions 180, each defining an alignment hole 182. The wide spacing of the holes, by nearly the length of the cathode sheets 50, provides rotational stability when the layers are stacked, even if there is slight looseness or positional error at the holes with respect to the alignment fixture.

Figure 11:
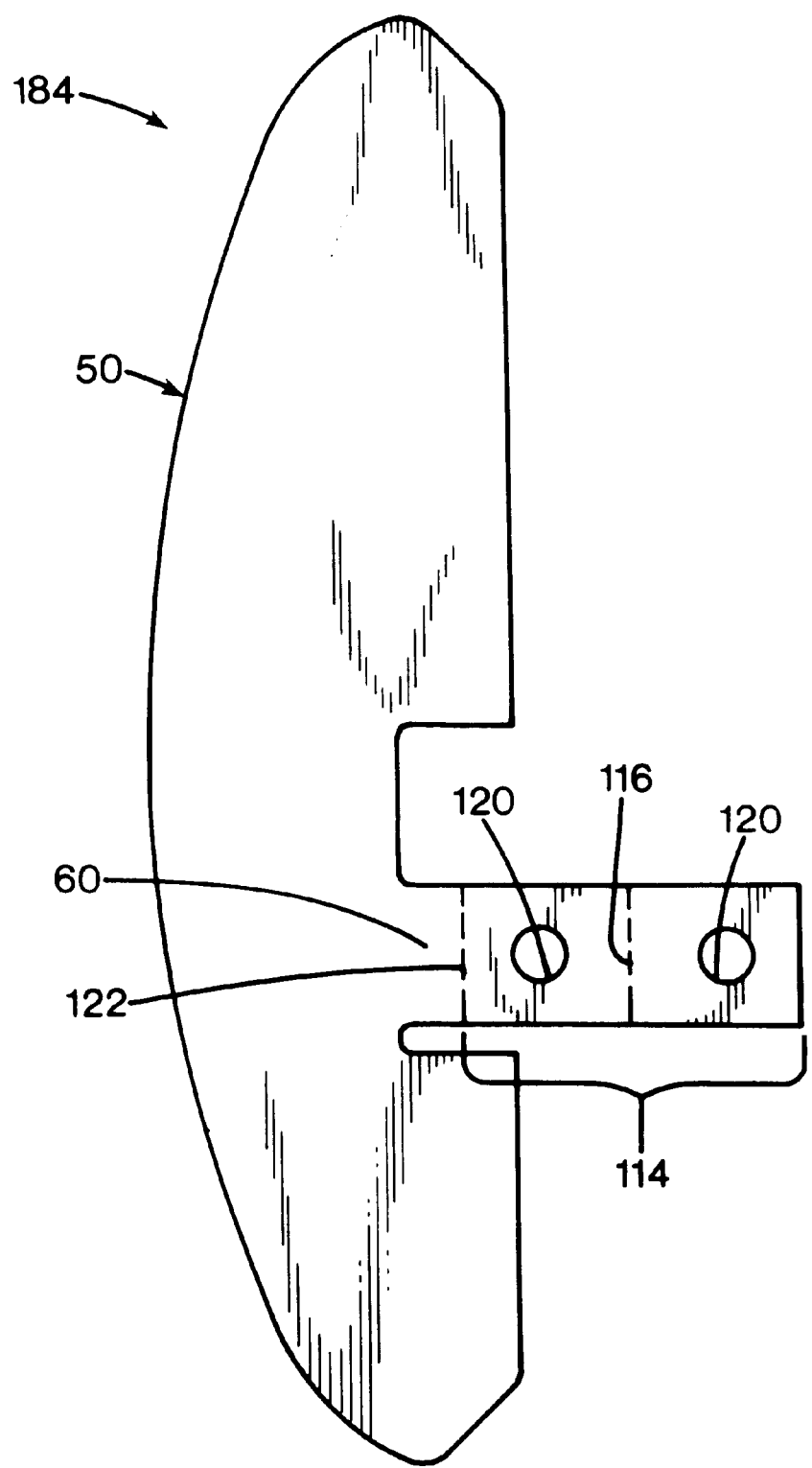
FIG. 11 is a plan view of a capacitor layer according to a second alternative embodiment of the invention.

In the embodiment of FIG. 11, only a single anode sheet portion 50 is provided on a single anode sheet 184. The sacrificial portion 114 is the same as in the preferred embodiment, with two alignment holes 120.

While the invention is described in terms of a preferred embodiment, the following claims are not intended to be so limited. For instance, the principles of the embodiments shown if FIGS. 10 and 11 may be combined for a single part layer with widely spaced apart alignment holes. Also, these principles may be applied to the cathode and insulating layers.

We claim:

1. A method of manufacturing a layered capacitor comprising the steps:
    forming a plurality of conductive sheets for use in a capacitor, each of the sheets having a profile including a sacrificial tab extending peripherally from the sheet;
    defining in each sacrificial tab at least a first alignment figure;
    stacking the sheets;
    aligning the profiles of the stacked sheets with each other by aligning the alignment figures of each sacrificial tab;
    removing the sacrificial tab from each of the sheets; and
    positioning the aligned stacked sheets in a capacitor housing.

2. The method of claim 1 including the step of securing the aligned stacked sheets to each other.

3. The method of claim 1 wherein forming a plurality of conductive sheets includes forming each sheet having a first sheet portion and a second sheet portion, and a sacrificial tab connected integrally between the first sheet portion and the second sheet portion, and wherein aligning the stacked sheets comprises forming a first stack of the first sheet portions and a second stack of the second sheet portions.

4. The method of claim 3 wherein positioning the stacked sheets in a capacitor housing includes positioning the first stack in a first capacitor housing, and positioning the second stack in a second capacitor housing.

5. The method of claim 1 including securing the stacked sheets to each other while removing the sacrificial portions by melting some of the sacrificial tabs.

6. The method of claim 5 wherein said securing step includes laser welding the sheets together.

7. The method of claim 1 wherein stacking the sheets includes interleaving a second set of conductive sheets between the sheets to provide interleaved anodes and cathodes.

8. A method of manufacturing capacitors comprising the steps:
    forming a plurality of conductive sheets, each sheet having a first portion, a second portion, and a sacrificial portion connected integrally between the first portion and the second portion;
    defining in each sacrificial portion of each sheet at least a first alignment figure; stacking the sheets;
    aligning the sheets by aligning the alignment figures with each other whereby the first portions comprise a first stack and the second portions comprise a second stack;
    removing the sacrificial portion from each of the sheets; and
    positioning each stack in a respective capacitor housing.

9. The method of claim 8 wherein said forming step includes forming the first portion and second portion as mirror images of each other.

10. The method of claim 8 wherein defining the alignment figure includes forming a hole.

11. The method of claim 8 wherein defining the alignment figure includes forming at least two spaced apart figures.

12. The method of claim 8 including the step of securing the sheets of each stack to each other.

13. The method of claim 8 wherein aligning the sheets includes providing an alignment fixture having an alignment element, and aligning the alignment figures with the alignment element.

14. The method of claim 13 wherein the step of defining in each sacrificial portion of each sheet at least a first alignment figure includes forming at least a first hole in each sacrificial portion, and the alignment element is a pin sized to be closely received in the holes.

15. A method of manufacturing a layered capacitor comprising the steps:
    forming a plurality of conductive sheets for use in a capacitor, each of the sheets having a profile including at least two spaced apart sacrificial portions contiguous with a sheet portion;
    defining in each sacrificial portion at least a first alignment figure;
    stacking the sheets to provide stacked sheet portions and stacked sacrificial portions with corresponding ones of the sacrificial portions being aligned with one another in a stacked relationship;
    aligning the sheet portions of each of the sheets by aligning the alignment figures of the sacrificial portions with each other;
    removing the sacrificial portions from each of the sheet portions; and
    positioning the stacked sheet portions in a capacitor housing.

16. A method of manufacturing capacitors comprising the steps:

forming a plurality of conductive sheets, each sheet having a first portion, a second portion, and at least two spaced apart sacrificial portions connected integrally between the first portion and the second portion;

defining in each sacrificial portion at least one alignment figure;

stacking the sheets;

aligning the sheets by aligning the alignment figures with each other such that the first portions comprise a first stack and the second portions comprise a second stack;

removing the sacrificial portion from each of the sheets; and positioning each stack in a respective capacitor housing.

* * * * *